United States Patent [19]

Black

[11] Patent Number: 4,597,764
[45] Date of Patent: Jul. 1, 1986

[54] OSSICULAR REPLACEMENT PROSTHESIS

[76] Inventor: Bruce Black, 73 Wickham Terrace, Brisbane, Australia

[21] Appl. No.: 655,622

[22] Filed: Sep. 28, 1984

[30] Foreign Application Priority Data

Sep. 28, 1983 [AU] Australia ............................... PG1604
Oct. 7, 1983 [AU] Australia ............................... PG1734

[51] Int. Cl.⁴ ............................ A61F 2/18; A61F 2/28
[52] U.S. Cl. .......................................... 623/10; 623/16
[58] Field of Search ..................... 3/1.9, 1; 623/10, 11, 623/16

[56] References Cited

U.S. PATENT DOCUMENTS 3,909,852 10/1975 Homsy ...................................... 3/1.9
4,281,419 8/1981 Treace ...................................... 3/1.9
4,510,627 4/1985 Treace et al. ........................... 623/10

FOREIGN PATENT DOCUMENTS 651804 3/1979 U.S.S.R. ................................. 623/10

Primary Examiner—Ronald L. Frinks
Attorney, Agent, or Firm—Kimmel, Crowell & Weaver

[57] ABSTRACT

Ossicular replacement prostheses have heads of dome-like, mushroom-like, or irregular elliptoid, shapes which bear against the tympanic membrane of the ear to provide a large area of contact between the heads and membrane even when the prosthesis are tilted through large angles. The hollow shaft of the partial prosthesis receives the head of the stapes, while the solid shaft of the total prosthesis engages the base or footplate of the stapes of the ear.

6 Claims, 14 Drawing Figures

OSSICULAR REPLACEMENT PROSTHESIS

BACKGROUND OF THE INVENTION (1) Field of the Invention

This invention relates to improvements in ossicular replacement prosthetises.

(2) Prior Art

In the middle ear a chain of three small bones called the hammer (malleus), the anvil (incus) and the stirrup (stapes) in the tympanic cavity, transmit the sound (in the form of vibrations) from the eardrum to the oval window (fenestra ovalis) in the membrane separating the middle ear from the inner ear.

This chain can become broken (e.g. due to injury) or be incomplete (e.g. due to a congenital defect) and so the hearing of the person may be wholly or partially impaired.

To overcome this problem, surgeons have implanted partial ossicular replacement prostheses (P.O.R.P.) or total ossicular replacement prostheses (T.O.R.P.) in the middle ear, dependent on whether or not the stapes (stirrup) is intact, to permit sound to travel from the eardrum to the inner ear.

While such prostheses have provided a partial solution to the problem, they generally have flat tops or caps which bear against the tympanic membrane of the eardrum. If the prostheses becomes tilted or partially dislodged, the edge of the top or cap creates a pressure point on the membrane and may result in permanent damage to the membrane.

SUMMARY OF THE PRESENT INVENTION

It is an object of the present invention to provide either a total or partial prosthesis where the top or cap has a curved upper surface which bears on the tympanic membrane of the eardrum to avoid any pressure points on the membrane.

It is a preferred object to provide such a cap which conforms to the shape of the membrane to provide a good working contact between the eardrum and the prosthesis.

It is a further preferred object to provide a prosthesis which will remain operational through a wide range of tilting displacements due e.g. to malpositioning, drum contraction or sneezing or coughing.

It is a still further preferred object to provide a partial prosthesis which provides optimal cover for the stapes and a good lever action.

Other preferred objects will become apparent from the following description.

In one aspect the present invention resides in a partial or total ossicular replacement prosthesis including:

a shaft or stem to be operably connected to, or engaged with, the stapes or membrane separating the middle and inner ears; and a head or cap on the shaft or stem to be operably engaged with the eardrum; wherein:

the head or cap has a substantially dome-like, mushroom-like, or irregular-elliptoid, shape in all three directions to maintain contact between the head or cap and the eardrum through a range of tilting displacements between the prosthesis and the eardrum.

Preferably the curvature of the head or cap corresponds to the curvature of the tympanic membrane to provide a large contact area between the prosthesis and the eardrum.

Preferably the partial prosthesis (P.O.R.P.) has a hollow shaft, the bore of which is open at its lower end to receive and engage the head of the stapes.

Preferably the total prosthesis (T.O.R.P.) has a solid shaft, the lower end of which is adapted to engage the base or footplate of the stapes—this prosthesis is used when the head or crura of the stapes are missing or irrepairably damaged.

The prostheses may be manufactured from "Plastipore" (trade mark) which is an ultra high molecular weight polyethrylene, which is approximately 70–90% porous. ("Plastipore" is a trade mark of the Richards Manufacturing Co., of Memphis, Tenn., U.S.A.).

Other suitable materials include bio-inert ceramics (e.g. sold under the trade mark "Macor" by Richards Manufacturing Co.); bio-inert calcium phosphate; hyaluronic acid; chondroitin sulphate or porous polysulfone.

BRIEF DESCRIPTION OF THE DRAWINGS

To enable the invention to be fully understood, a number of preferred embodiments will now be described with reference to the accompanying drawings, in which.

DETAILED DESCRIPTION OF THE PREFERRED EMBODIMENT

Figure 1:
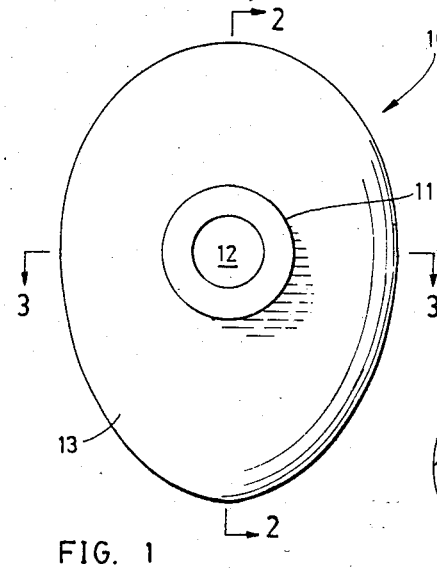
FIG. 1 is an underside view of a first embodiment of the partial prosthesis.
Figure 2:
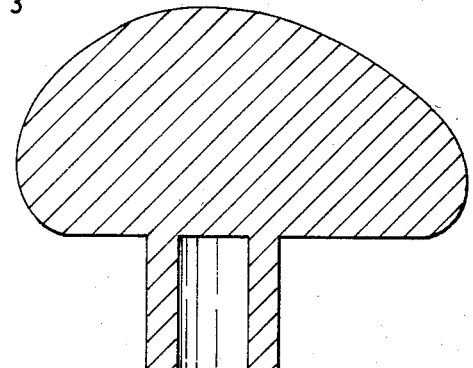
FIGS. 2 and 3 are respective cross-sectional views of the prosthesis taken on lines 2—2, 3—3 respectively of FIG. 1, (the stapes being shown in dashed lines in FIG. 3)
Figure 3:
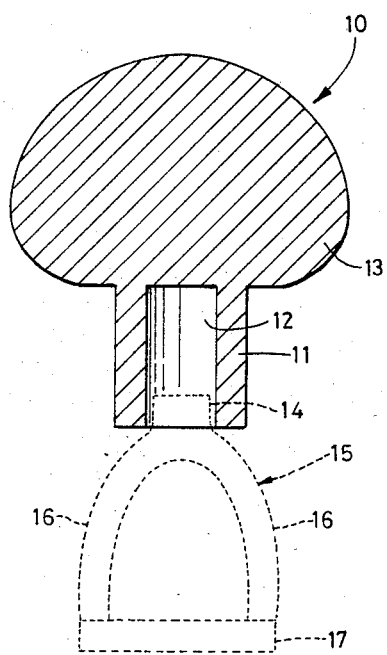
Figure 4:
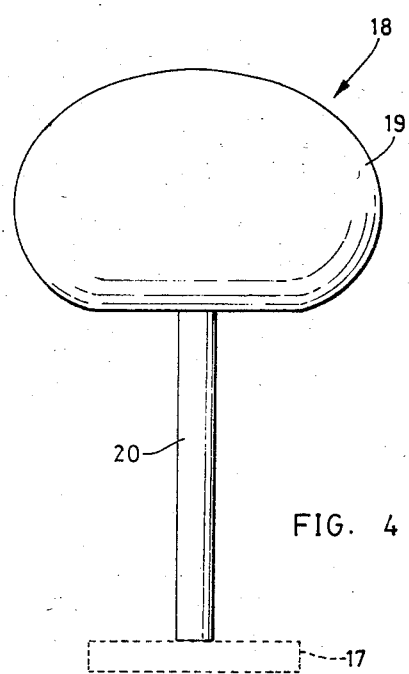
FIG. 4 is a side view of the total prosthesis having the same head or cap shape as the partial prosthesis of FIGS. 1 to 3.

Referring to FIGS. 1 to 3, the partial prosthesis (P.O.R.P.) 10 is manufactured from "Plastipore" (trade mark) polyethylene and has a shaft 11 with a central bore 12 open at its lower end. A head or cap 13 is formed integrally with the shaft 11 and has the irregular elliptoid shape shown in the figures. As shown, the head 13 is substantially elliptical or ovoid in plan view, with a complex curved outer face and a substantially planar underside. The outer face of the head substantially conforms to the shape of the tympanic membrane of the eardrum to provide a large contact area therebetween and has large radius corners to prevent the development of pressure points on the membrane which could form sites of breakdown of the membrane.

As shown in FIG. 3, the head 14 of the stapes 15 engages in the bore 12 of the shaft 11 and the sound is transmitted from the prosthesis to the inner ear via the crura 16 and footplate 17 of the stapes.

When only the footplate 17 of the stapes 15 remains in the middle ear, the total prosthesis (T.O.R.P.) 18 is used. This has a head 19 of the same shape and configuration as the head 13 of the partial prosthesis 10. However, it has a thin solid shaft 20 (e.g. which may be 6 mm. long compared to the 3 mm. long shaft 11), which engages the footplate 17 of the stapes.

Figure 5:
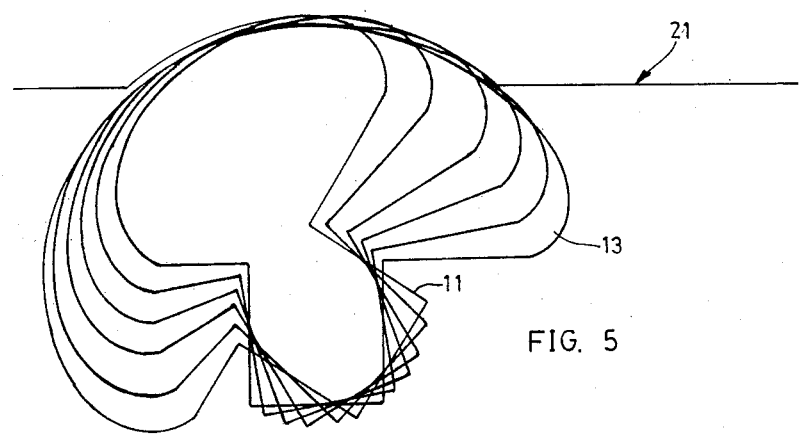
FIGS. 5, 6 and 7 show the range of tilt of the partial prosthesis upwards, downwards and sideways, respectively, where contact is maintained between the prosthesis and the eardrum.
Figure 6:
Figure 7:
Figure 8:
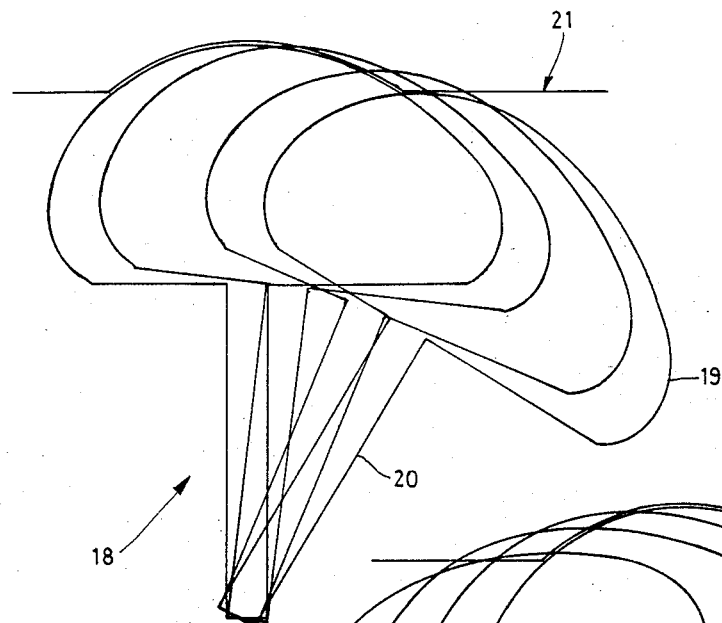
FIGS. 8, 9 and 10 show the range of tilt for the total prosthesis downwards, upwards and sideways respectively, where contact is maintained between the prosthesis and the eardrum.
Figure 9:
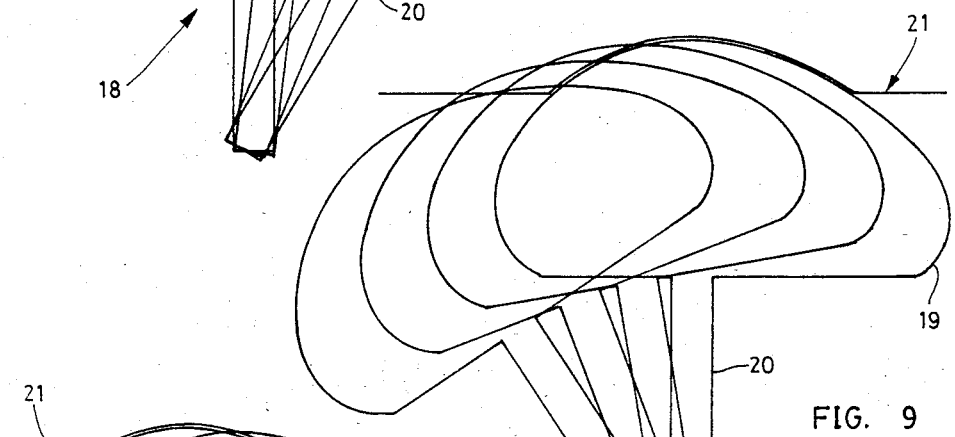
Figure 10:
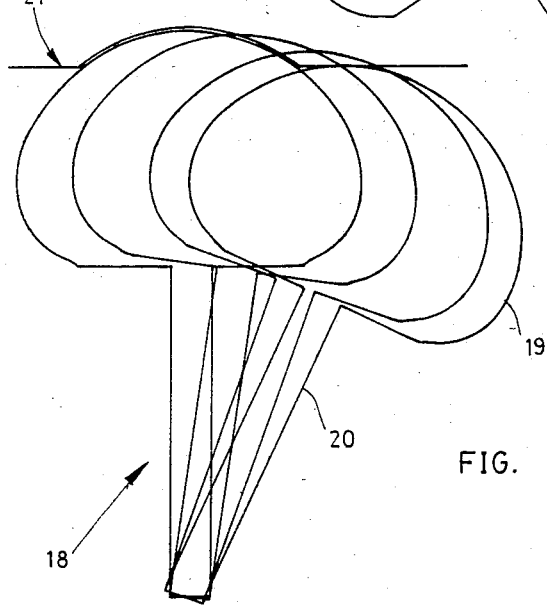

Because of the complex shape of the heads 13, 19 of the prosthesis 10, 18 the prosthesis will remain in operational contact with the tympanic membrane of the eardrum 21 through a wide range of tilting displacements, as shown in FIGS. 5 to 7 for the partial prosthesis 10 and FIGS. 8 to 10 for the total prosthesis 18.

Figure 11:
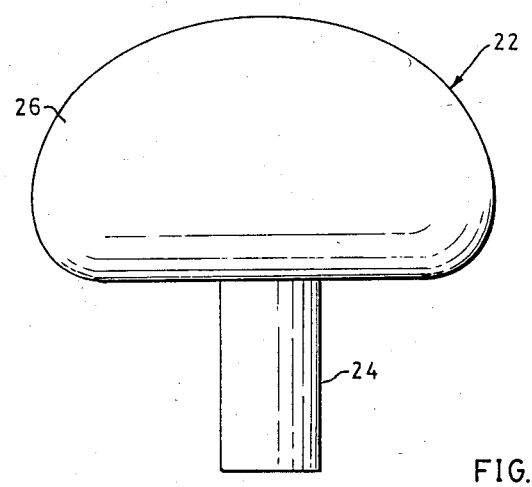
FIG. 11 is a side view of a second embodiment of the total prosthesis.
Figure 12:
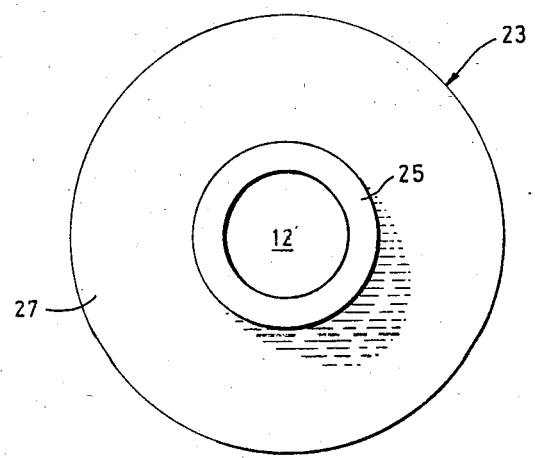
FIG. 12 is an underside view of a second embodiment of the partial prosthesis having the same head or cap shape
Figure 13:
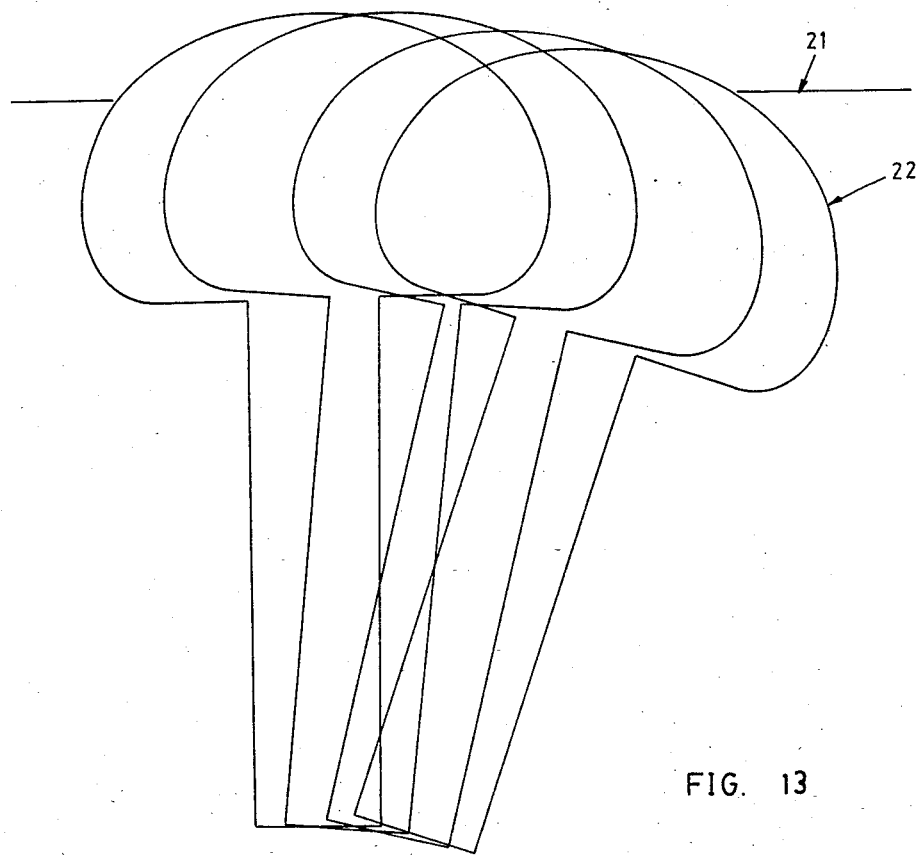
FIGS. 13 and 14 show the range of tilt respectively, of the total or partial prosthesis of FIGS. 11 and 12.
Figure 14:
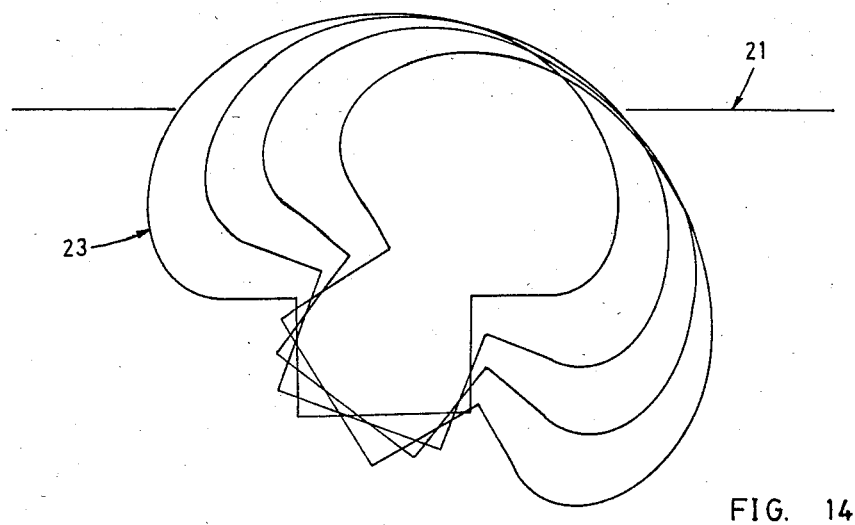

Referring to FIGS. 11 and 12, the total and partial prostheses, 22, 23 respectively, have shafts 24, 25 corresponding to the shafts 20, 11 of the prostheses 18, 10 of FIGS. 1 to 10. However, the heads 26, 27 of each prosthesis is of substantially mushroom shape with a substantially hemi-spherical or domed outer face connected to a substantially planar underside by large radius corners (see FIG. 11). The outer face of the heads substantially conforms to the shape of the tympanic membrane and as shown in FIGS. 13 and 14, the heads 26, 27 maintain contact with the tympanic membrane through a wide range of tilting displacements.

In both embodiments of the invention, a one-piece ossicular prosthesis is provided which includes a shaft portion and a substantially enlarged head or cap 13, FIG. 1, or 26, FIG. 11. In each case, the head or cap is smoothly rounded on its end face which engages and conforms to the shape of the tympanic membrane of the eardrum to provide a large contact area therewith. The curved face of the head or cap of the prosthesis has a compound curvature across the head or cap on two orthogonal axes and on a third axis longitudinally of the shaft of the prosthesis. The interior or underside of the head or cap is essentially flat as shown in FIGS. 2 and 11.

The arrangement enables the use of a one-piece prosthesis which can maintain good conforming contact with the tympanic membrane even when the prosthesis is tilted through rather large angles in any direction.

The invention ensures evenly distributed pressure of the head or cap on the tympanum, and avoids a concentration of pressure at a local point on the membrane, as might be caused by a flat plate-like head or cap.

The particular shape and size of the prostheses may be changed to suit the particular intended applications and other variations and modifications may be made to the embodiments described without departing from the scope of the present invention as defined in the appended claims.

I claim:

1. A replacement ossicular prosthesis comprising a shaft portion adapted for connection with the stapes of the middle ear, and a substantially enlarged head attached to one end of the shaft portion and projecting radially thereof in all directions and having a substantially flat interior surface adjacent to the shaft portion and having an exterior smoothly rounded tympanic membrane engaging surface, said engaging surface having compound curvature on at least two axes of the enlarged head and serving to maintain a large area of contact with the tympanic membrane through a substantial range of tilting of the prosthesis relative to the eardrum.

2. A replacement ossicular prosthesis as defined in claim 1, and the compound curvature of the engaging surface of the head corresponding substantially to the natural curvature of the tympanic membrane.

3. A replacement ossicular prosthesis as defined in claim 1, and the enlarged head being symmetrical about the longitudinal axis of the shaft portion and having the general shape of a mushroom.

4. A replacement ossicular prosthesis as defined in claim 1, and the enlarged head being non-symmetrical about the longitudinal axis of the shaft portion and having the general shape of a truncated irregular elliptoid.

5. A replacement ossicular prosthesis as defined in claim 1, and the shaft portion being hollow and having a bore adapted to receive the head of the stapes.

6. A replacement ossicular prosthesis as defined in claim 1, and the shaft portion being solid and elongated and being adapted to engage the base of the stapes.

* * * * *